US012678253B2

(12) United States Patent
Kimpton et al.

(10) Patent No.: US 12,678,253 B2
(45) Date of Patent: *Jul. 14, 2026

(54) DRAPE INTERFACE STRUCTURE

(71) Applicant: CMR Surgical Limited, Cambridge (GB)

(72) Inventors: Laura Saranne Kimpton, Baldock (GB); Thomas Edward Parker, London (GB)

(73) Assignee: CMR Surgical Limited, Cambridge (GB)

( * ) Notice: Subject to any disclaimer, the term of this patent is extended or adjusted under 35 U.S.C. 154(b) by 180 days.

This patent is subject to a terminal disclaimer.

(21) Appl. No.: 18/472,674

(22) Filed: Sep. 22, 2023

(65) Prior Publication Data

US 2024/0099798 A1     Mar. 28, 2024

(30) Foreign Application Priority Data

Sep. 23, 2022     (GB) ..................................... 2213927

(51) Int. Cl.
A61B 46/10        (2016.01)
A61B 46/00        (2016.01)
(52) U.S. Cl.
CPC .............. *A61B 46/10* (2016.02); *A61B 46/40* (2016.02)
(58) Field of Classification Search
CPC .......... B24J 19/00; A61B 34/30; A61B 34/00; A61B 34/70; A61B 1/00135; A61B 1/00142; A61B 2090/0813; A61B 90/08; A61B 46/00; A61B 46/10; A61B 46/23; A61B 17/00

USPC ...... 700/245; 901/49–50; 600/121, 124–125; 606/130; 128/849–856
See application file for complete search history.

(56) References Cited

U.S. PATENT DOCUMENTS

| | | | |
|---|---|---|---|
| 2009/0248039 A1* | 10/2009 | Cooper .................. | A61B 34/30 |
| | | | 128/849 |
| 2024/0099803 A1* | 3/2024 | Kimpton ............... | A61B 46/10 |

FOREIGN PATENT DOCUMENTS

| | | | | |
|---|---|---|---|---|
| GB | 2538230 A | 11/2016 | | |
| GB | 2570518 A | * 7/2019 | ............. | A61B 46/10 |
| WO | 2016081286 A1 | 5/2016 | | |
| WO | WO-2018141783 A1 | * 8/2018 | ........ | A61M 25/0009 |

OTHER PUBLICATIONS

WO 2018141783 A1 machine translation (Year: 2018).*
Combined Search and Examination Report Under Sections 17 and 18(3) for UK Patent Application No. GB2213927.3, mailed Feb. 23, 2023.

* cited by examiner

*Primary Examiner* — Caitlin A Carreiro
(74) *Attorney, Agent, or Firm* — Andrus Intellectual Property Law, LLP

(57)        ABSTRACT

A drape interface structure including a frame defining an opening, a membrane spanning the opening of the frame, and a drive transfer element attached to the membrane and adapted to convey motion through the membrane. The membrane is of a material that can deform to form a plastically deformed region in the membrane in response to an initial movement of the drive transfer element relative to the frame, such that subsequent movements of the drive transfer element in the membrane have reduced resistance from the membrane.

18 Claims, 8 Drawing Sheets

DRAPE INTERFACE STRUCTURE

CROSS-REFERENCE TO RELATED APPLICATION

This application claims priority to GB Patent Application No. 2213927.3, filed Sep. 23, 2022, which is incorporated herein by reference in its entirety.

FIELD OF THE DISCLOSURE

This invention relates to an interface structure which provides a sterile barrier. In one embodiment, the structure has a thin membrane, retained in a frame and covering an opening defined by the frame. The membrane may be capable of plastically deforming without tearing or detaching from the frame, meaning that a barrier is maintained, and no contaminants can pass through. The interface structure may have at least one drive transfer element retained in the membrane. Each drive transfer element may be adapted to convey motion through the structure.

BACKGROUND

In a surgical environment, it is particularly important that any components that cannot readily be disinfected between procedures are prevented from becoming contaminated during an operation.

Robots have become increasingly prevalent for use in surgical procedures. A surgical robotic assembly comprises a base which supports the robot, an arm and an instrument. The arm extends between the base and instrument. There is an interface between the instrument and the arm; at this interface, various instruments can be releasably connected to the arm and a driving mechanism in the arm can be used to manipulate the distal end of the instrument.

It is typically impractical to sterilise the base and arm of a robotic assembly without damaging the mechanical components and the large size presents further challenges when disinfecting and sterilising. As an alternative to disinfection and sterilisation, covering a surgical robot with a disposable covering is an effective barrier to prevent contamination. A surgical drape is a covering which envelops the base and arm of a surgical robot to separate a sterile field from an operative area where surgery is performed by the instrument.

At the interface between the robotic arm and instrument, the two components can suitably engage with each other so that the instrument is supported and can articulate to perform or assist with a surgical procedure. There is a need for an improved interface structure which can convey motion from the robotic arm to the instrument through a barrier during a surgical procedure while maintaining sterility.

SUMMARY OF THE INVENTION

According to a first aspect of the present invention there is provided a drape interface structure comprising a frame defining an opening; a membrane spanning the opening of the frame, and a drive transfer element attached to the membrane and adapted to convey motion through the membrane. The membrane is of a material that may deform to form a plastically deformed region in the membrane in response to an initial movement of the drive transfer element relative to the frame, such that subsequent movements of the drive transfer element in the membrane have reduced resistance from the membrane.

The membrane may be substantially taut such that the drive transfer element is held in the membrane The membrane may deform, in response to the initial movement of the drive transfer element a distance along a drive path, to form the plastically deformed region having a length along the drive path of at least half of the distance moved along the drive path.

The membrane may deform, in response to the initial movement of the drive transfer element along a drive path, to form the plastically deformed region having a width perpendicular to the drive path of at least the width of the drive transfer element.

The membrane may deform, in response to the initial movement of the drive transfer element, to form the plastically deformed region such that the membrane surrounding the plastically deformed region is not plastically deformed.

The membrane may deform such that the subsequent movements of the drive transfer element in the plastically deformed region have substantially no resistance from the membrane.

The membrane may deform such that the subsequent movements of the drive transfer element in the plastically deformed region have reduced resistance from the membrane A drape interface structure may comprise one or more further drive transfer elements, each further drive transfer element being attached to the membrane and adapted to convey motion through the membrane.

One or more further drive transfer elements may be adapted to convey motion through the membrane along respective drive paths, and the respective drive paths of the drive transfer elements may be parallel to one another.

The membrane may deform to form respective further plastically deformed regions in the membrane in response to an initial movement of each of the further drive transfer elements relative to the frame, such that subsequent movements of each of the further drive transfer elements in the membrane have reduced resistance from the membrane.

The membrane may deform, in response to the initial movement of each of the drive transfer elements, to form the respective plastically deformed regions such that the respective plastically deformed regions do not overlap.

The membrane may deform, in response to the initial movement of each of the drive transfer elements, to form the respective plastically deformed regions such that the respective plastically deformed regions do overlap.

According to a second aspect of the present invention there is provided a drape interface structure comprising a frame defining an opening, a membrane spanning the opening of the frame, and a drive transfer element attached to the membrane and adapted to convey motion along a drive path through the membrane. The membrane may be configured to have a lower resistance on the movement of the drive transfer element in a direction along the drive path and a higher resistance on the movement of the drive transfer element in a direction not along the drive path.

The membrane may comprise a material that is configured to have a lower resistance on the movement of the drive transfer element in a direction along the drive path and a higher resistance on the movement of the drive transfer element in a direction not along the drive path.

The membrane may comprise an anisotropic material.

The membrane may comprise a structure that is configured to have a lower resistance on the movement of the drive transfer element in a direction along the drive path and a higher resistance on the movement of the drive transfer element in a direction not along the drive path.

The membrane may be configured to have a highest resistance on the movement of the drive transfer element in a direction perpendicular to the drive path.

The membrane may be configured to have an increasing resistance on the movement of the drive transfer element with respect to the angle of the direction of the movement of the drive transfer element from the drive path.

The drape interface structure may comprise one or more further drive transfer elements, each further drive transfer element being attached to the membrane and adapted to convey motion through the membrane along a respective drive path.

The respective drive paths of the drive transfer elements may be parallel to one another.

The membrane may be configured to have a lower resistance on the movement of each of the further drive transfer elements in a direction along the respective drive paths and a higher resistance on the movement of each of the further drive transfer elements in a direction not along the respective drive paths.

The drive transfer element may comprise a recess on a first side of the membrane and a protrusion on the second side of the membrane.

The drive transfer element recess may be engageable with an interface protrusion, and the drive transfer element protrusion may be engageable with an interface recess.

The frame may comprise a securing fittings for securing the frame to a robot arm.

The drive path may be linear.

The frame and the drive transfer element may be heat welded to the membrane.

The material of the membrane may be a thermoplastic polymer.

The thermoplastic polymer material of the membrane may comprise one or more of high-density polyethylene or linear low-density polyethylene.

The material of the one or more drive transfer elements may comprise a non-elastomeric material.

The material of the one or more drive transfer elements may comprise polyethylene.

The material of the frame may comprise polyethylene.

DETAILED DESCRIPTION

The following description is presented to enable any person skilled in the art to make and use the invention, and is provided in the context of a particular application. Various modifications to the disclosed embodiments will be readily apparent to those skilled in the art.

Figure 1:
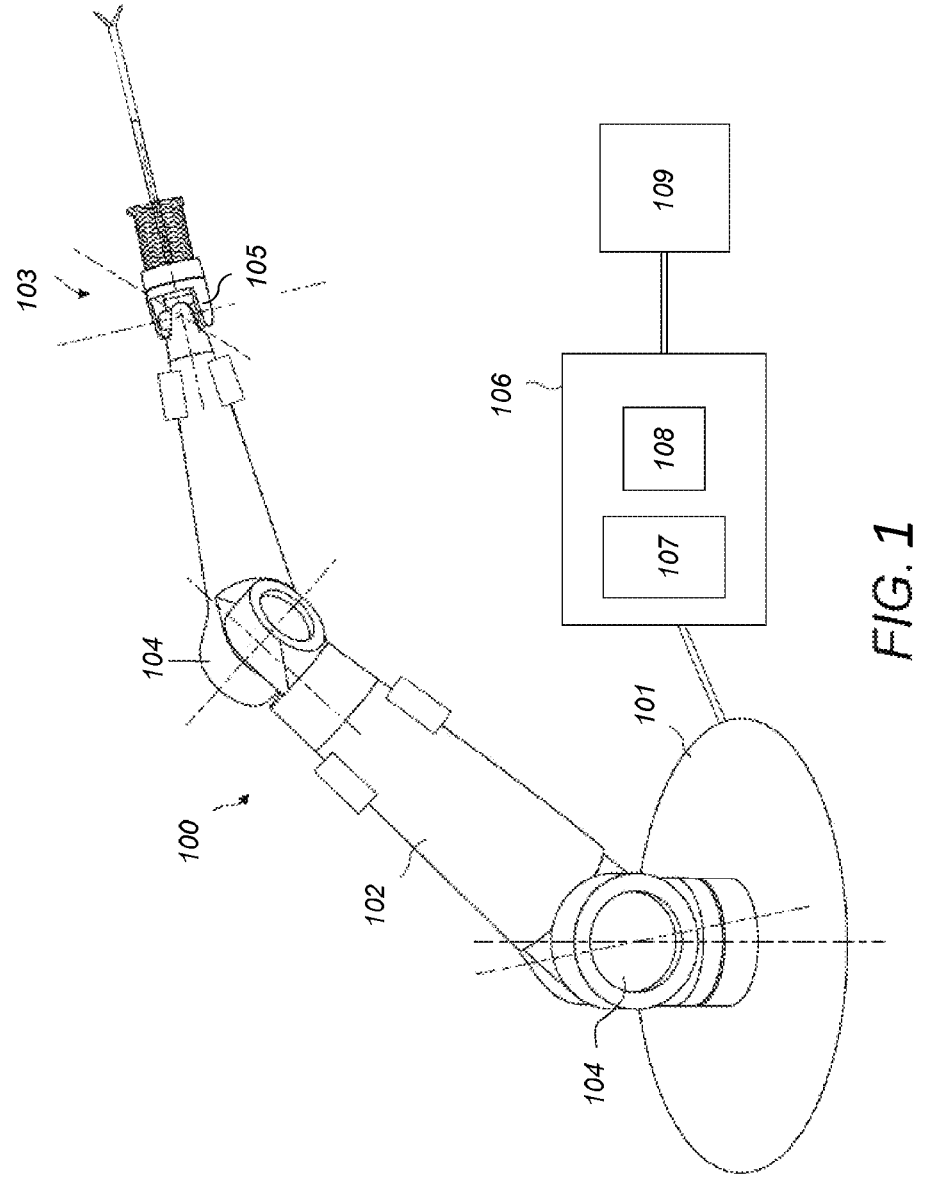
FIG. 1 illustrates a surgical robot and associated control system.

FIG. 1 shows a typical surgical robot 100 and associated control system 106. A base 101 is shown which supports an arm 102 and an instrument 103. The base provides stability by, for example, being rigidly attached to an operating theatre floor or attached to a trolley. The arm 102 is articulated by means of multiple flexible joints 104 along its length, used to position the instrument 103 in a suitable location for performing surgery. A surgical drape (not shown) may be attached at the interface 105 between the instrument 103 and arm 100. The surgical instrument 103 is connected at the distal end of the robot arm 102, it may be releasably attached.

The control system 106 includes a surgeon command interface 109 where commands are input. The control system 106 comprises a processor 107 and a memory 108. The control system 106 is coupled to motors for driving motion of a drive assembly to articulate the instrument 103.

Figure 2:
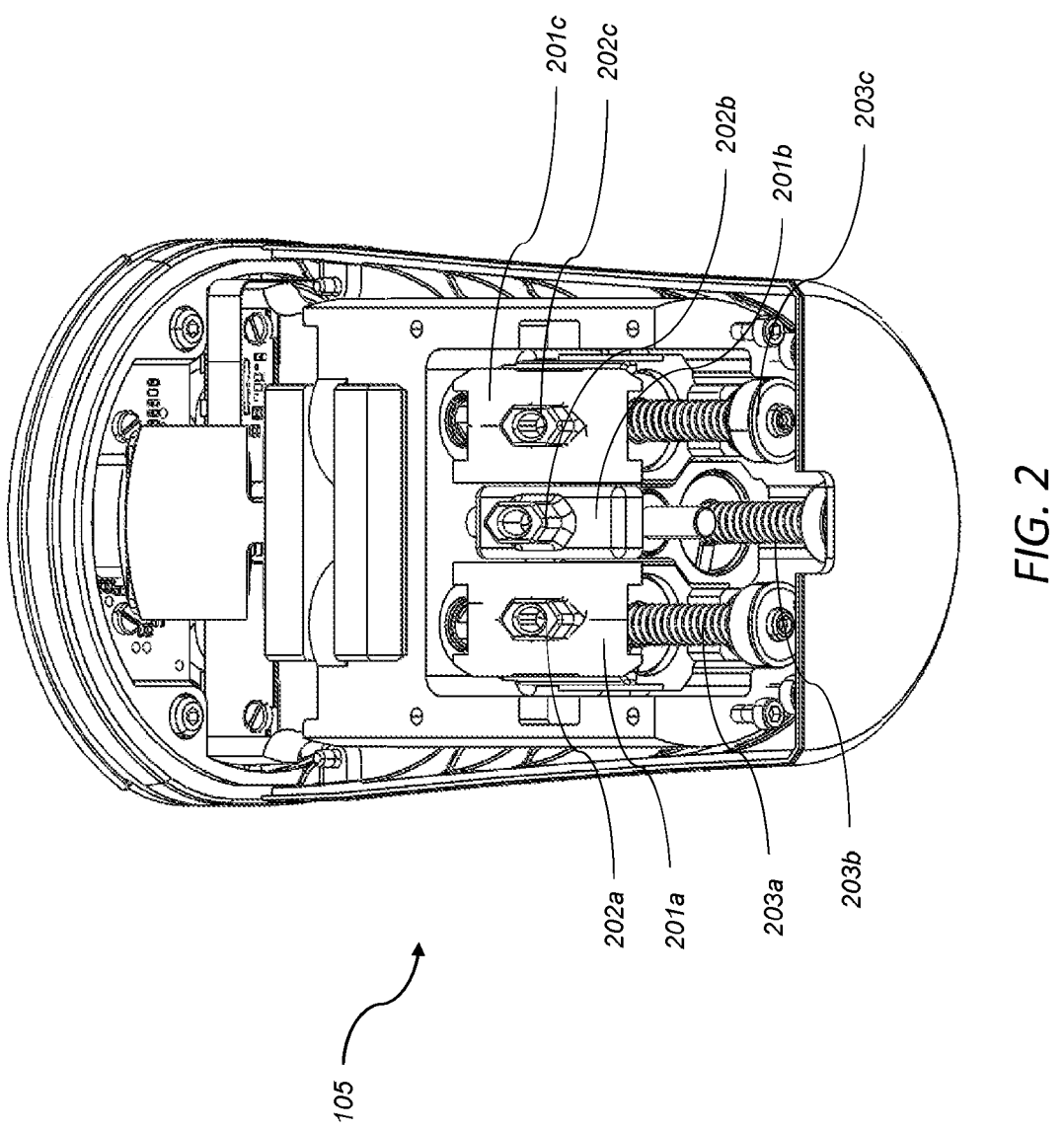
FIG. 2 illustrates the interface of a surgical robot arm.

A surgical robot arm 102 interface 105 is illustrated in FIG. 2. The interface 105 comprises one or more robot arm interface elements 201. FIG. 2 shows three robot arm interface elements 201a, 201b, 201c. However, it will be appreciated that there may be a different number of robot arm interface elements 201a, 201b, 201c depending on the requirements on the driving structure. For example, the number of degrees of freedom of the instrument 103 may determine the number of drive inputs required which may in tern determine the number of robot arm interface elements 201a, 201b, 201c.

The robot arm interface elements 201a, 201b, 201c are shown to comprise interface features 202a, 202b, 202c. The robot arm interface features 202a, 202b, 202c are suitable for engaging with corresponding features in the instrument 103. FIG. 2 shows that the robot arm interface features 202a, 202b, 202c comprise interface protrusions 202a, 202b, 202c. However, it will be appreciated that the robot arm interface features 202a, 202b, 202c may additionally or alternatively comprise interface recesses 202a, 202b, 202c. The selection of a protrusion or recess may depend on the requirements of the drive system, and the features present in the instrument 103. The robot arm interface features 202a, 202b, 202c are located on the robot arm interface elements 201a, 201b, 201c. For example, the robot arm interface features 202a, 202b, 202c may extend out of, for protrusions, or extend into, for recesses, the robot arm interface elements 201a, 201b, 201c.

In FIG. 2, the robot arm interface elements 201a, 201b, 201c are driven by respective lead screws 203a, 203b, 203c. The lead screws 203a, 203b, 203c may rotate along a female threaded elements engaged with the lead screws 203a, 203b, 203c. This causes the female threaded elements to move along the lead screws 203a, 203b, 203c. The result is that the lead screws 203a, 203b, 203c may provide the robot arm interface elements 201a, 201b, 201c with linear drive. However, it will be appreciated that there may be different ways of driving the robot arm interface elements 201a, 201b, 201c, which may result in different types of drive. For example, the robot arm interface elements 201a, 201b, 201c may be provided with rotational or irregular non-linear drive.

Figure 3:
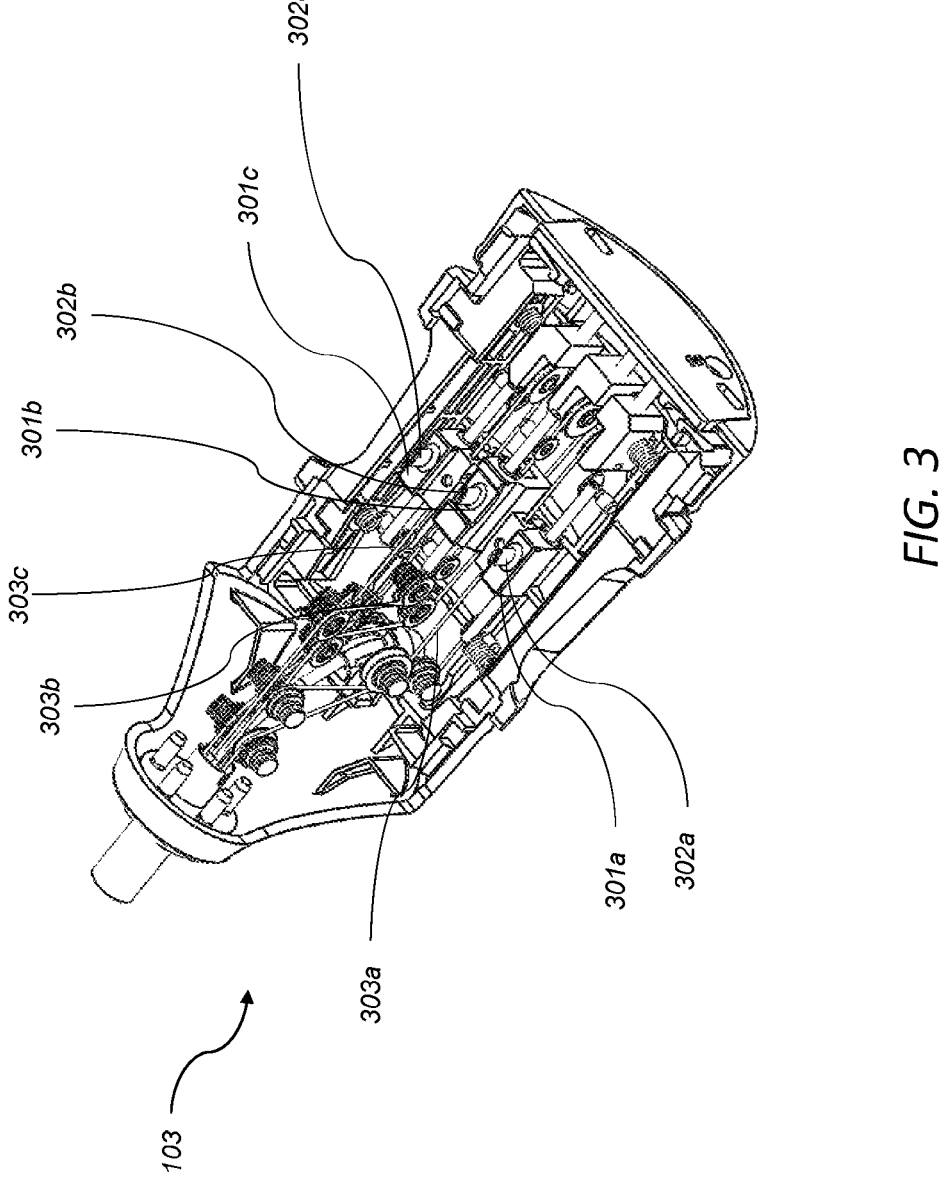
FIG. 3 illustrates the interface of a surgical instrument.

A surgical instrument 103 is illustrated in FIG. 3. The instrument 103 comprises one or more instrument interface elements 301. FIG. 3 shows three instrument elements 301a, 301b, 301c. However, it will be appreciated that there may be a different number of instrument elements 301a, 301b, 301c depending on the requirements on the driving structure. For example, the number of degrees of freedom of the instrument 103 may determine the number of drive inputs required which may in tern determine the number of instrument interface elements 301a, 301b, 301c.

The instrument interface elements 301a, 301b, 301c are shown to comprise interface features 302a, 302b, 302c. The instrument interface features 302a, 302b, 302c are suitable for engaging with corresponding features in the robot arm 102. FIG. 3 shows that the instrument interface features 302a, 302b, 302c comprise interface protrusions 302a, 302b, 302c. However, it will be appreciated that the instrument interface features 302a, 302b, 302c may additionally or alternatively comprise interface recesses 302a, 302b, 302c. The selection of a protrusion or recess may depend on the requirements of the drive system, and the features present in the robot arm 102. The instrument interface features 302a, 302b, 302c are located on the instrument interface elements 301a, 301b, 301c. For example, the instrument interface features 302a, 302b, 302c may extend out of, for protrusions, or extend into, for recesses, the instrument interface elements 301a, 301b, 301c.

In FIG. 3, the instrument interface elements 301a, 301b, 301c drive instrument cables 303a, 303b, 303c. The instrument interface elements 301a, 301b, 301c are connected to the instrument cables 303a, 303b, 303c and slide along straight bars. The result is that the instrument interface elements 301a, 301b, 301c may provide the instrument cables 303a, 303b, 303c with linear drive. However, it will be appreciated that there may be different ways of driving the instrument cables 303a, 303b, 303c, which may result in different types of drive. For example, the instrument cables 303a, 303b, 303c may be provided with rotational or irregular non-linear drive. The instrument cables 303a, 303b, 303c are used to control the end effector elements of the instrument 103.

Figure 4:
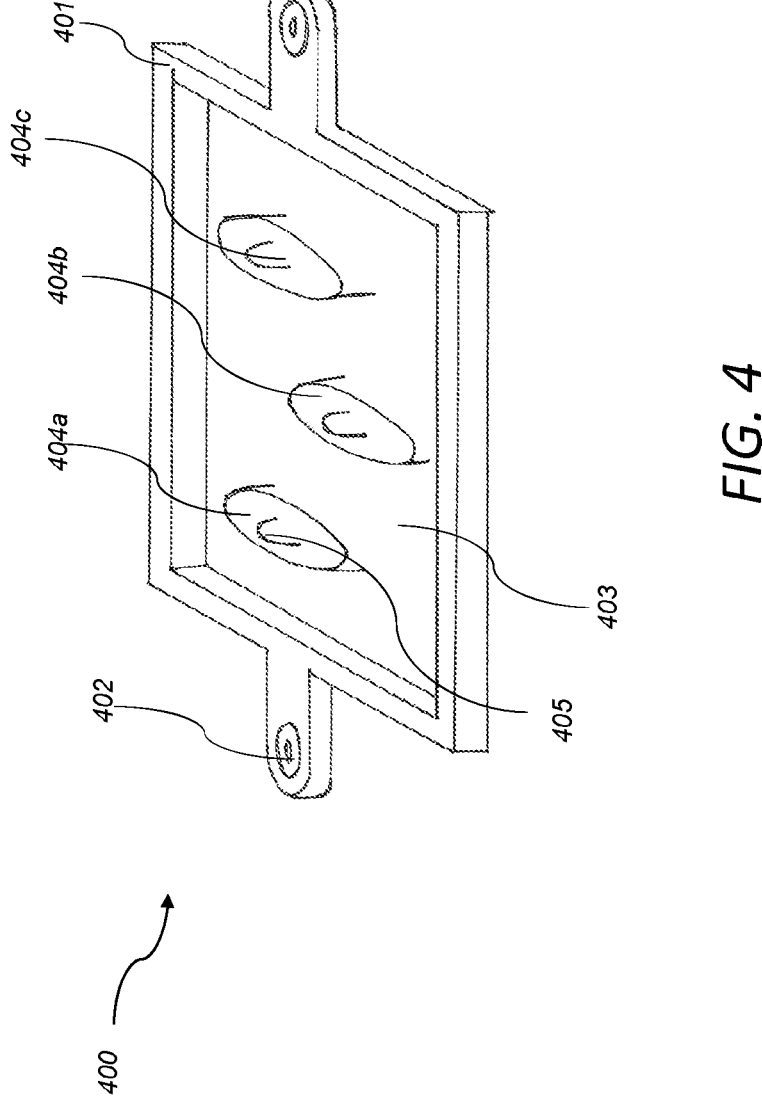
FIG. 4 illustrates a perspective view of a drape interface structure.
Figure 5:
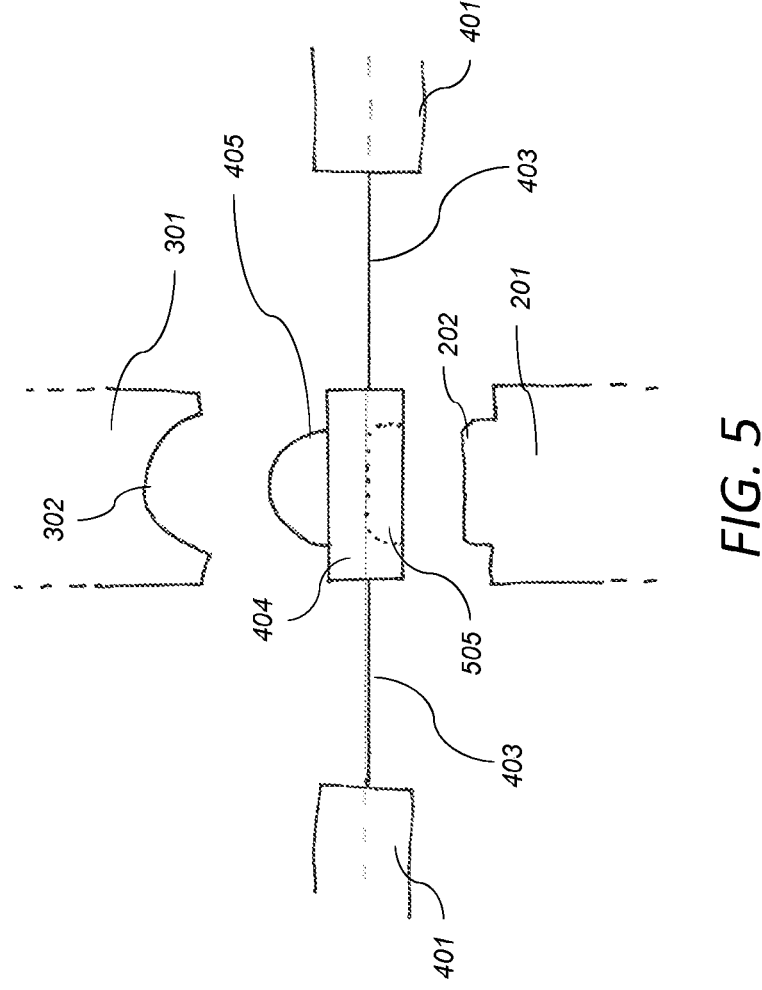
FIG. 5 illustrates a cross-sectional view of a drive transfer element.

A drape interface structure of all embodiments is illustrated in FIGS. 4 and 5.

FIG. 4 shows the drape interface structure 400. The drape interface structure 400a comprises a frame 401. As shown in FIG. 4, the frame 401 comprises a substantially rectangular profile. However, other shapes for the frame 401 may be suitable, such as round shapes. Additionally, the edges of the frame 401 may be chamfered, rounded, or notched. In any event, the frame 401 preferably is shaped to fit with the structure to which it is attached. The frame 401 may also be a rigid frame. In other words, the frame 401 may substantially maintain its shape when under loading during operation. Alternatively, the frame 401 may not be a rigid frame. For example, the frame 401 may be provided by a drape surrounding the drape interface structure 400.

The frame 401 may comprise a non-elastomeric material. In this way, the frame 401 may comprise the rigid structure which may substantially maintain its shape when under loading during operation. In particular, the frame 401 may comprise a polyolefin material, such as polyethylene or polypropylene. Additionally, the frame 401 may be made from more than one material. For example, the frame 401 may be made from high density polyethylene (HDPE) with a styrene-ethylene-butylene-styrene (SEBS) coating.

The outer edge of the frame 401 (the sides opposing the opening) may be attached to a surgical drape (not shown in the Figures). This surgical drape may be used to cover at least the arm 102 of the surgical robot 100. The drape interface structure 400 may be retained within the drape or connect to it. In an embodiment, the surgical drape is attached to the drape interface structure 400. A technician, surgeon or nurse may position the drape interface structure 400 between the robotic arm 102 and robotic instrument 103 prior to a surgical procedure. The drape interface structure 400 may be disconnected after a surgical procedure.

The frame 401 defines an opening. As shown in FIG. 4, the opening is substantially rectangular. However, other shapes for the frame 401 may be suitable, such as round shapes. The opening is covered by a membrane 403. The membrane 403 spans the opening of the frame 401. In particular, the membrane 403 spans the full area of the opening such that there is a sterile barrier formed.

The membrane 403 may be heat welded to the frame 401. The membrane 403 may be chemically bonded to the frame 401, for example with adhesive. The membrane 403 may comprise a thermoplastic polymer. The membrane may comprise polyethylene. The membrane may comprise an aligned polymer film. In particular, the membrane 403 may comprise high-density polyethylene. Alternatively, or in addition, the membrane 403 may comprise linear low-density polyethylene. A single material or a combination of materials may be used in the membrane 403 to give the desired properties.

Thermoplastics are capable of being heated to a softened state and reshaped. Thermoplastic components may be well-suited to repeated processing and thermal attachment to other components. Several versatile manufacturing methods are commonly used to process thermoplastics such as injection moulding, blow moulding, and casting. Thermoplastic sheets are produced industrially by first blending the necessary raw materials, then heating and pressing through an extrusion die, then the extruded plastic is drawn into a sheet by the pressure applied between rollers. Several sets of rollers or multiple passes through rollers may be used to draw the sheet to a specific thickness while the thermoplastic is warm. Finally, the sheet is cooled and can then be cut to a desired size and shape.

Polyethylenes are a group of polymers with the chemical formula $(C_2H_4)_n$ as the repeat unit. The mechanical properties of polyethylene are influenced by the molecular weight and the extent of branching; highly branched polyethylene has a higher density and typically has a higher percentage crystallinity, meaning it is typically more brittle.

HDPE is made up of linear chains with less branching than the short branches in linear low-density polyethylene (LLDPE). Puncture-resistant thin films of LLDPE are readily processed. LLDPE has a structure composed of many short, branched chains, these branches have a low degree of cross linking between the chains so, in response to an applied tensile stress, the chains are free to slide over each other without becoming entangled. LLDPE has a low dispersity (a narrow distribution of molecular weight) so a higher degree of crystallinity can be achieved. LLDPE has similar strength to HDPE but is more flexible. Use of LLDPE for the material of the membrane 403 may provide good strength and flexibility.

The membrane 403 may have a thickness of less than 1 mm. The elongation at break of the film may be more than 600%. The density the film at room temperature may be 0.97 g/cm$^3$ plus or minus 10%. The elongation at break of the film may be more than 400%. If the film is an aligned film the elongation at break may be 1400% or more in the alignment direction The frame 401 comprises securing fittings securing fittings 402 for securing the frame 401 to a structure. Preferably, the securing fittings 402 are capable of securing the frame 401 to the robot arm 102. In particular, the securing fittings 402 are capable of securing the frame 401 to the interface 105 of the robot arm 102. The securing fittings 402 may comprise a click-in lock, magnets, screws, or any other suitable types of securing fittings 402. The securing fittings 402 are capable of engaging with a corresponding feature on the robot arm 102. The securing fittings 402 may be a surface relief. As shown in FIG. 4, the securing fittings 402 are positioned on a fin which extends away from the opening of the frame 401. There may be more than one securing fittings 402. FIG. 4 shows two securing fittings 402 which are located on opposite sides of the frame 401. However, the number, and location, of securing fittings 402 may be varied depending on the force requirements on the securing fittings 402. An operator, prior to a procedure, can position the frame 401 to releasably attach to an arm 102 and on the opposing side of the frame 401 releasably attach to an instrument 103.

As shown in FIG. 4, the drape interface structure 400 comprises a drive transfer element 404. The drive transfer element 404 is attached to the membrane 403. In other words, the drive transfer element 404 may be a separate component to the membrane 403 and attached thereto. The drive transfer element 404 may be heat welded to the membrane 403. The drive transfer element 404 may be chemically bonded to the membrane 403, for example with adhesive. The membrane 403 may be formed from a flat sheet with holes cut out such that the membrane 403 is attached to the sides of the drive transfer element 404. Alternatively, the flat sheet of the membrane 403 could be bonded to the top or bottom surface of the drive transfer element 404. Alternatively, the membrane 403 may be over moulded to the drive transfer element 404. The membrane 403 may be substantially taut. In this way, the drive transfer element 404 may be held in the membrane 404.

In an alternative embodiment, the membrane 403 may be joined to the frame 401 and drive transfer element 404 by laser welding. In a further alternative embodiment, the membrane 403 may have a backing film which is adhered to a surface of the membrane 403 to improve the bonding with the rigid parts and reinforce the membrane 403. Lamination of polymer layers may be used to form a membrane 403.

The drape interface structure 400 may further comprise a reinforcement member in the membrane 403. The reinforcement member may be adjacent to the drive transfer element 404. For example, the reinforcement member may comprise a ring which surrounds the drive transfer element 404. The reinforcement member may comprise a different material to the membrane 403. The reinforcement member may comprise a stiffer and/or stronger material than the membrane 403. The reinforcement member may provide additional strength to the membrane 403 in the region where the membrane 403 and the drive transfer element 404 connect. In a region of the membrane 403 surrounding the drive transfer element 404 the shear forces may be higher. In this way, the reinforcement member may reduce the likelihood of tearing of the membrane 403 in the region surrounding the drive transfer element 404.

Polyethylene (PE), which as described herein the membrane 403 may be manufactured from, is non-polar and may not readily react with solvents, meaning that adhesives and solvents may not be appropriate for joining PE parts to each other. Heat welding of PE parts is a simple and effective method of joining, which involves overlaying the parts to be attached and applying heat to soften the thermoplastic. An infrared emitter may be used to weld the membrane to the frame 401 and to the drive transfer element 404. The thin membrane layer is suited to attachment by heat welding because it transmits heat well and melts to bond to a substrate. The strength of an attachment made by heat welding parts varies with the temperature used and the materials selected. A higher seal initiation temperature is needed for HDPE than LLDPE: HDPE melts in the temperature range 126° C. to 135° C., LLDPE melts in the temperature range 115° C. to 160° C. In this way, an LLDPE membrane 403 may have a lower seal initiation temperature.

The heat welding process fixes the membrane 403 to the rigid parts and a barrier to contaminants is produced. The frame 401 and drive transfer elements 404a, 404b, 404c may be made of the same material, for example a polymer, metal, or composite. The frame 401 and drive transfer element 404 may be made of dissimilar materials. A non-elastomer such as PE may be used to form the rigid parts.

The drive transfer element 404 is adapted to convey motion through the membrane 403. The drive transfer element 404 may move with respect to the frame 401 in the membrane 403. The membrane 403 may be flexible such that the drive transfer element 404 may move within the opening of the frame 401.

The drive transfer element 404 may move along a drive path. The drive path may be a linear path. The drive path may be a circular path. The drive path may be irregular with linear and curved sections. In this case of linear drive paths, the drive path may follow a drive axis. The drive path may be determined by the structure that is driving the drive transfer element 404.

As shown in more detail in FIG. 5, the drive transfer element 404 may comprise a recess 505 on a first side of the membrane 203. In particular, the drive transfer element recess 505 may be engageable with an interface protrusion 202. The first side of the membrane 403 may, for example, face the robot arm 102. In this case, the interface protrusion 202 is located on an interfacing element 201 of the robot arm 102. Alternatively, the first side of the membrane 403 may face the instrument 103. In this case, the interface protrusion 202 is located on an interfacing element 201 of the instrument 103. As shown in FIG. 5, the drive transfer element recess 505 may comprise a concave or semi-circular shape. In 3D this may provide a hemispherical recess. The interface protrusion 202 may comprise a corresponding shape, for example the convex or semi-circular shape. In 3D this may provide a hemispherical protrusion. This curved shape, or any other form of tapered shape, may provide self-locating when the interface protrusion 202 is engaged with the drive transfer element recess 505. However, it will be appreciated that other shapes may be suitable depending on the locating and loading requirements on the drive structure. For example, the drive transfer element recess 505 may comprise a pyramid shape, a rectangular shape, or a cylindrical shape. It is preferable that the shape of the drive transfer element recess 505 and the interface protrusion 202 correspond to one another. In other words, the interface protrusion 202 should fit in the drive transfer element recess 505. Preferably, the fit between the interface protrusion 202 and the drive transfer element 505 should be a snug, or an interference fit.

The drive transfer element 404 may comprise a protrusion 405 on a second side of the membrane 403. In particular, the drive transfer element protrusion 405 may be engageable with an interface recess 302. The second side of the membrane 403 may, for example, face the instrument 103. In this case, the interface recess 302 is located on an interfacing element 301 of the instrument 103. Alternatively, the second side of the membrane 403 may face the robot arm 102. In this case, the interface recess 302 is located on an interfacing element 301 of the robot arm 102. As shown in FIG. 5, the drive transfer element protrusion 405 may comprise a convex or semi-circular shape. In 3D this may provide a hemispherical protrusion. The interface recess 302 may comprise a corresponding shape, for example the concave or semi-circular shape. In 3D this may provide a hemispherical recess. This curved shape, or any form of tapered shape, may provide self-locating when the drive transfer element protrusion 405 is engaged with the interface recess 302. However, it will be appreciated that other shapes may be suitable depending on the locating and loading requirements on the drive structure. For example, the drive transfer element protrusion 405 may comprise a pyramid shape, a rectangular shape, or a cylindrical shape. It is preferable that the shape of the interface recess 302 and the drive transfer element protrusion 405 correspond to one another. In other words, the drive transfer element protrusion 405 should fit in the interface recess 302. Preferably, the fit between the drive transfer element protrusion 405 and interface recess 302 should be a snug, or an interference fit.

In alternative embodiments, the drive transfer element 404 may comprise a recess 505 on both sides of the membrane 403, or the drive transfer element 404 may comprise a protrusion 405 on both sides of the membrane 403. In any event, the drive transfer element 404 may be provided with a suitable number and arrangement of recesses 505 and protrusions 405 depending on the structure of the robot arm 102 and instrument 103 on either side of the drive transfer element 404.

The drive transfer element 404 may comprise a non-elastomeric material. The material properties of the drive transfer element 404 may be stiffer than the membrane 403. In this way, the drive transfer element 404 may comprise the rigid structure which may substantially maintain its shape when under loading during operation. In particular, the drive transfer element 404 may comprise a polyethylene material. The drive transfer element 403 may comprise more than one material. For example, the drive transfer element 403 may comprise a stiffer core and a less stiff coating. In this way, the core may provide the rigid structure, and the coating may provide good adhering properties for connecting to other components. The drive transfer element 404 may be formed by moulding, casting and/or milling. In the case of milling, CNC milling may be used to form the drive transfer element protrusion 406 and/or drive transfer element recess 405.

As shown in FIG. 4, the drape interface structure 400 may comprise more than one drive transfer element 404. FIG. 4 shows three drive transfer elements 404a, 404b, 404c. It will be appreciated that there may be a different number of drive transfer elements 404a, 404b, 404c depending on the requirements on the driving structure. Each of the drive transfer elements 404a, 404b, 404c are attached to the membrane 403. Each of the drive transfer elements 404a, 404b, 404c may be heat welded to the membrane 403.

As seen in FIG. 4, the opening of the frame defines a window in a notional coordinate system where the opening extends in the x and y directions. The area of the window is relatively larger than the drive transfer elements 404a, 404b, 404c, such that a plurality of drive transfer elements 404a, 404b, 404c can fit within the window. A section of membrane 403 cut from a larger sheet has an area at least the size of the window, and may have an excess edge to attach to the frame. In the coordinate system, the motion of the drive transfer elements 404a, 404b, 404c may be a translation in the x, y, z direction, or some combination of these, the motion may also be a rotation.

Each of the drive transfer elements 404a, 404b, 404c are adapted to convey motion through the membrane 403. Each of the drive transfer elements 404a, 404b, 404c may move with respect to the frame 401 in the membrane 403. Each of the drive transfer elements 404a, 404b, 404c may move independently with respect to one another. The membrane 403 may be flexible such that each of the drive transfer elements 404a, 404b, 404c may move within the opening of the frame 401.

Each of the drive transfer elements 404a, 404b, 404c may move along a respective drive path. The respective drive paths may be a linear path. The respective drive paths may be circular paths. The respective drive paths may be irregular with linear and curved sections. In this case of linear drive paths, the drive path may follow a drive axis. The respective drive paths may be next to one another. In the case of linear drive paths, the respective drive paths may be parallel to one another. In the case of curved or non-linear drive paths, the respective drive paths may maintain a constant distance to one another such that they are parallel at any individual point along the path. The respective drive paths may be determined by the structure that is driving each of the drive transfer elements 404a, 404b, 404c.

Figure 6:
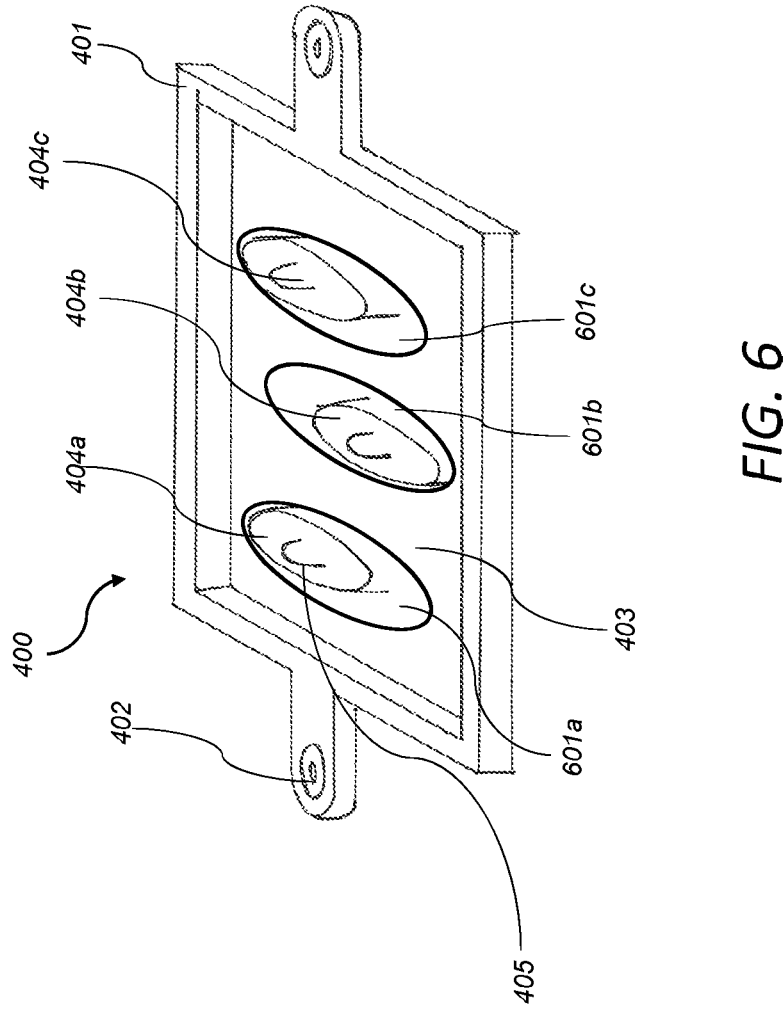
FIG. 6 illustrates a perspective view of a drape interface structure of a first embodiment.

One embodiment of the invention is illustrated in FIGS. 6 and 7.

As shown in FIGS. 4 and 6, the drive transfer element 404 is surrounded by the membrane 403 and held within the membrane 403. In this way, the drive transfer element 404 may be held in an initial position. In the initial position, the drive transfer element 404 is supported by the tension in the membrane 403. The membrane 303 is in a strained state in which tensile forces from the membrane 403 hold the drive transfer element 404 in place. In implementations where the membrane 403 is planar, this may hold or support the drive transfer element 404 substantially in the plane of the membrane 403. The drive transfer element 404 preferably moves in the plane of the membrane 403, rather than out of the plane of the membrane 403. In this way, the tension in the membrane 403 may be reduced.

Any movement of the drive transfer element 404 in the membrane 403 would need to overcome the tension provided by the membrane 403. As such, driving the drive transfer element 404 in the membrane 403 would need significant force. The tension force from the membrane 403 can also be inconsistent. High and/or inconsistent tension force from the membrane 403 can add additional loading on the driving elements and can make it difficult to control the position of the driving elements. The increased loading on the drive transfer elements can also result in less cable tension in the instrument 103 for a given motor torque. Additionally, increasing the tension in the membrane 403 can increase the likelihood of tearing of the membrane 403. The tension can be particularly high when two drive transfer elements 404 are at opposite ends of travel, or are both a long way from their respective starting positions. Alternatively, tension can be particularly high in rotary drive when drive transfer elements 404 turn by a large angle. It can therefore be advantageous to reduce the level of tension in the membrane 403.

As described herein, the drive transfer element 404 can be driven within the membrane 403. As the membrane 403 is constrained by the frame 401, movements in the membrane 403 are movements relative to the frame 401. The membrane 403 can plastically deform in response to the drive transfer element 404 moving within the membrane 403. In particular, an initial movement of the drive transfer element 404 causes the membrane 403 to form a plastically deformed region 601 in the membrane 403. The plastically deformed region 601 is illustrated in FIG. 6. The plastically deformed region 601 may include the part of the membrane 403 in which the drive transfer element 404 has initially moved around in. Alternatively, or additionally, the plastically deformed region 601 may be outside of the part of the membrane 403 in which the drive transfer element 404 has initially moved around in. The plastic deformation is a permanent deformation. As such, the plastically deformed region 601 may only be increased in size, and not decreased by subsequent movements of the drive transfer element 400. Notwithstanding that there may be chemical or mechanical processes in which it is possible to reverse the deformation. The deformation may be permanent in such a way that the deformation may not be reversed easily in normal operation, or by the surgical system alone.

In response to the initial movement of the drive transfer element 404, the membrane 403 may provide a reduced resistance on subsequent movements of the drive transfer element 404. The plastically deformed region 601 of the membrane 403 provides a region of reduced resistance. Any subsequent movements of the drive transfer element 404 in the membrane 403 may have a reduced level of resistance. In the case of the plastically deformed region 401 being formed in the region of initial movements, any subsequent movements of the drive transfer element 404 in the plastically deformed region 601 may have a reduced level of resistance. A reduced level of resistance may be interpreted as the plastically deformed region 601 of the membrane 403 providing a lower level of resistance on the drive transfer element 404 than before the plastically deformed region 601 was formed. The reduced level of resistance may be due to the plastically deformed region 601 providing a significantly reduced level of tension force on the drive transfer element 404.

As illustrated in FIG. 6, the plastically deformed region 601 may surround the initial position of the drive transfer element 404. This may be because any initial movement of the drive transfer element 404 may produce a surrounding plastically deformed region 601. The perimeter of the plastically deformed region 601 may be defined by the maximum distance the drive transfer element 404 has moved from the initial starting point. In other words, any point in the membrane 403 to which the drive transfer element 404 has travelled my fall within the plastically deformed region 601.

However, due to tension in the membrane, and/or other factors, the plastically deformed region 601 may not perfectly match the points to which the drive transfer element 404 has travelled. The membrane 403 may more readily deform in regions which are under higher stress during the movement of the drive transfer element 404. Correspondingly, the membrane 403 may less readily deform in regions which are under lower stress during the movement of the drive transfer element 404. The plastically deformed region 601 may be smaller or larger than the points to which the drive transfer element 404 has travelled. For example, if the drive transfer element 404 moves towards the edge of the membrane 403, then the tension at that point may be high, and the plastically deformed region 601 may not reach the extreme point of travel. In another example, as the drive transfer element 404 moves, the plastically deformed region 601 may be wider that the width of the drive transfer element 404. This may be because tension on the membrane 403 either side of the drive transfer element 404 may cause the plastically deformed region 601 to expand sideways.

The membrane 403 may comprise a homogeneous structure. The deformation regions 601 of a membrane 403 with a homogeneous structure may directly correspond to the regions of stress in the membrane during movement of the drive transfer element 404. This is because the variation in deformation may only be as a result of the variation in stress across the membrane 403. As a result, the plastically deformed region 601 may not perfectly match the points to which the drive transfer element 404 has travelled. Alternatively, the membrane 403 may comprise a non-homogeneous structure. For example, the membrane 403 may comprise a non-uniform thickness. The membrane 403 may comprise thicker regions and thinner regions. The thinner regions may be more likely to deform than the thicker regions. The membrane 403 may preferentially deform in thinner regions than in thicker regions. As another example, the membrane 403 may comprise a non-uniform deformability. The membrane 403 may comprise stiffer regions and less stiff regions. The less stiff regions may be more likely to deform than the stiffer regions. The membrane 403 may preferentially deform in stiffer regions than in less stiff regions. As a result, the deformation regions 601 of a membrane 403 with a non-homogeneous structure may not directly correspond to the regions of stress in the membrane during movement of the drive transfer element 404. This is because the variation in deformation is not only as a result of the variation in stress across the membrane 403 and may also be due to the variation in deformability across the membrane 403. As a result, the plastically deformed region 601 may not perfectly match the points to which the drive transfer element 404 has travelled.

Preferably, the membrane 403 surrounding the boundary of the plastically deformed region 601 is not plastically deformed. Plastically deforming the membrane 403 may cause the membrane 403 to be made thinner and/or slacker. In this way, the membrane 403 may be more susceptible to the sterile barrier being broken. It can be advantageous to keep the surround membrane 403 as not being plastically deformed such that the membrane 403 maintains the sterile barrier.

As described herein, the drive transfer element 404 may move along a drive path. The drive path may be a linear path. The drive path may be a circular path. The drive path may be irregular with linear and curved sections. In this case of linear drive paths, the drive path may follow a drive axis. The drive transfer element 404 may also convey rotational motion through the membrane 403. In this example, the drive transfer element 404 may not move along a drive path. Instead, the drive transfer element 404 may rotate around the stationary point. In another embodiment, the drive transfer element 404 may both rotate and travel along a drive path 404, such that the point of rotation also moves.

In response to an initial movement of the drive transfer element 404 along the drive path, the membrane 403 may form a plastically deformed region 601 which has a length of at least half of the distance moved along the drive path. In other words, if the drive transfer element 404 moves 20 mm along the drive path, then the plastically deformed region 601 will be at least 10 mm long. It will be appreciated that the dimensions are arbitrary, and are not necessarily representative of the drape interface structure 400 size. Preferably, the length of the deformed region 601 is as close as possible to the distance moved by the drive transfer element 404. In this way, the region of reduced resistance may be larger. In some embodiments, the deformed region 601 may cover the entire membrane 403. In this way, any subsequent movement of the drive transfer element 404 may have reduced resistance.

In response to an initial movement of the drive transfer element 404 along the drive path, the membrane 403 may form a plastically deformed region 601 which has a width of at least the width of the drive transfer element 404. In other words, if the drive transfer element 404 is 5 mm wide, then the plastically deformed region 601 will be at least 5 mm wide. It will be appreciated that the dimensions are arbitrary, and are not necessarily representative of the drape interface structure 400 or drive transfer element size. Preferably, the width of the deformed region 601 is significantly wider the width of the drive transfer element 404. In this way, the region of reduced resistance may be larger.

As described herein the plastically deformed region 601 is formed in response to an initial movement of the drive transfer element 404. The plastically deformed region 601 may be expanded by means of subsequent movements of the drive transfer element 404. For example, if, in a subsequent movement, the drive transfer element 404 moves beyond the boundary of the plastically deformed region 601, the plastically deformed region 601 may further increase in size. In this way, the region of reduced resistance may be increased. This may be advantageous if the normal operating drive path is due to increase.

As described herein the plastically deformed region 601 may provide a region of reduced resistance when compared to the resistance before the membrane 403 was plastically deformed. Preferably, the plastically deformed region 601 provides a region of significantly reduced resistance on the drive transfer element 404. For example, the level of resistance may be reduced by 50%. More preferably, the plastically deformed region 601 provides a region of substantially no resistance on the drive transfer element 404. This may be interpreted as an insignificant level of resistance when compared to the resistance before the membrane 403 was plastically deformed, or when compared to the forces used in driving the drive transfer elements 404.

The level of resistance on the drive transfer element 404 may not be constant over the plastically deformed region 601. For example, the level of resistance may be higher at or near the perimeter of the plastically deformed region 601. As such, it may be advantageous to carry out subsequent movements of the drive transfer element 404 within a subregion of the plastically deformed region 601. Put another way, it may be advantageous to make the plastically deformed region 601 slightly larger than the region in which the drive transfer element 404 will subsequently move.

A method for operating the surgical robot 100 to form the plastically deformed region 601 is included below. The control system 106 of the surgical robot 100 is configured to initially drive the drive transfer element 404 in the membrane 403 relative to the frame 401. The initial movement may be performed as part of a start up of the surgical robot 100. Alternatively, the initial movement may be performed in response to a new instrument 103 being attached to the robot arm 102. For example, this may be the first instrument 103 being attached during surgery. Moving the drive transfer element 404 may cause the membrane 403 to form a plastically deformed region 601 in the membrane 403. The plastically deformed region 401 may provide a region of reduced resistance on the drive transfer element 404. The control system 106 is configured to subsequently drive the drive transfer element 404 within the plastically deformed region 601. The control system 106 may drive the drive transfer element 404 by means of an interface element 201 on the robot arm 102. Additionally, the control system 106 may be configured to detect when the plastically deformed region 601 has been formed. For example, the control system 106 may comprise a sensor configured to monitor the resistance on the driving elements.

As described herein with reference to FIG. 4, the drape interface structure 400 may comprise more than one drive transfer element 404. FIG. 4 shows three drive transfer elements 404a, 404b, 404c. The membrane 403 is configured to plastically deform in response to each of the drive transfer elements 404a, 404b, 404c moving within the membrane 403. In particular, an initial movement of each of the drive transfer elements 404a, 404b, 404c causes the membrane 403 to form respective plastically deformed regions 601a, 601b, 601c in the membrane 403. The respective plastically deformed regions 601a, 601b, 601c are illustrated in FIG. 6. The respective plastically deformed regions 601a, 601b, 601c may include the parts of the membrane 403 in which each of the drive transfer elements 404a, 404b, 404c initially moved around in.

In response to the initial movement of each of the drive transfer elements 404a, 404b, 404c, the membrane 403 may provide a reduced resistance on subsequent movements of each of the drive transfer elements 404a, 404b, 404c. The respective plastically deformed regions 601a, 601b, 601c of the membrane 403 provide respective regions of reduced resistance. Any subsequent movements of each of the drive transfer elements 404a, 404b, 404c in the respective plastically deformed regions 601a, 601b, 601c may have a reduced level of resistance.

In some situations, it may be suitable for the respective plastically deformed regions 601a, 601b, 601c to not overlap. In this case, there may be a region which has not plastically deformed between each of the respective plastically deformed regions 601a, 601b, 601c. This may provide a stronger sterile barrier in between each of the drive transfer elements 404a, 404b, 404c. Alternatively, in other situations, it may be suitable for the respective plastically deformed regions 601a, 601b, 601c to overlap. In this case, the respective plastically deformed regions 601a, 601b, 601c may form a continuous plastically deformed region 601. A continuous plastically deformed region may provide reduced tension from the membrane 403 between the each of the drive transfer elements 404a, 404b, 404c. This may be advantageous when each of the drive transfer elements 404a, 404b, 404c are being driven independently, and possibly in different directions at different times.

Figures 7A, 7B:
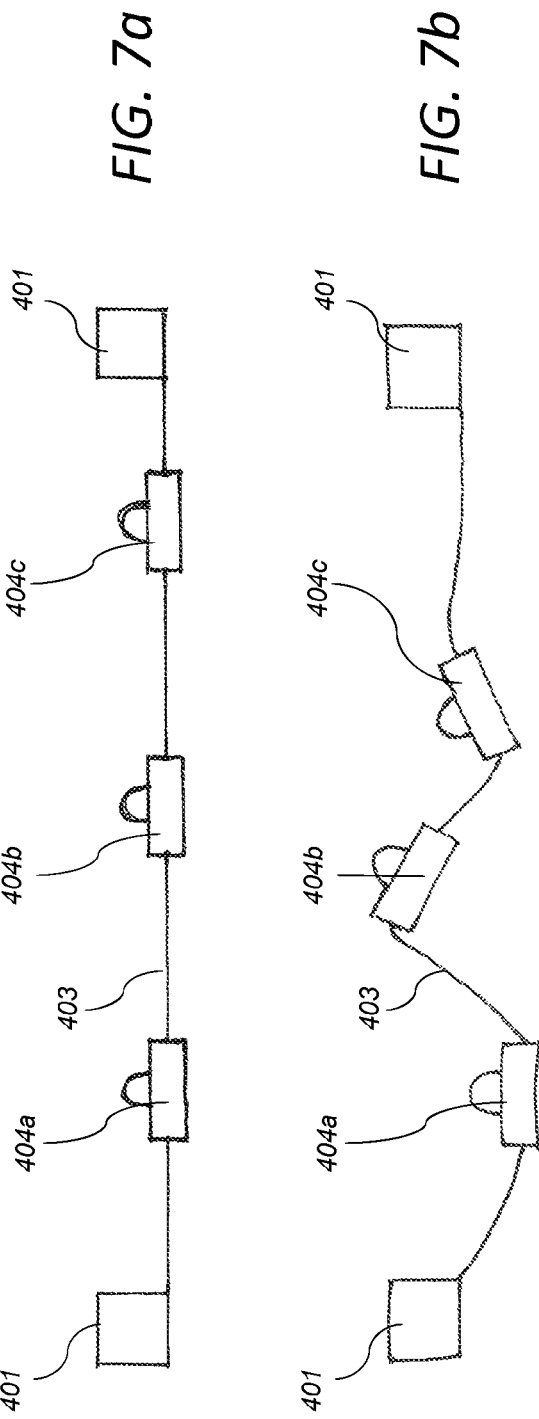
FIGS. 7a and 7b illustrate a cross-sectional view of the drape interface structure, before and after plastic deformation of the membrane, of the first embodiment.

FIGS. 7a and 7b show a side profile view of the structure seen in FIG. 6. FIG. 7a shows an initial position where the membrane 403 has not been plastically deformed and supports three drive transfer elements 404a, 404b, 404c. FIG. 7b shows a second position showing that the membrane 403 has been plastically deformed by the conveyed motion of at least one of the drive transfer elements 404a, 404b, 404c.

FIG. 7a shows two opposing sides of the frame 401 and the membrane 403 spanning between the sides. The drive transfer elements 404a, 404b, 404c are shown to have sides that are bonded to the membrane 403. The membrane 403 is shown to be substantially thinner than the side of the drive transfer elements 404a, 404b, 404c. As shown in FIG. 7b, once the membrane 403 has been plastically deformed, it may no longer provide tension to support the drive transfer elements 404a, 404b, 404c.

To allow for the deformation, the material of the membrane 403 has a high percentage strain-to-failure and low yield strength so the membrane 403 be elongated and permanently deformed while remaining as a continuous sheet between the rigid elements (frame 401 and the drive transfer elements 404a, 404b, 404c). Additionally, the material of the membrane 403 may have a low maximum tensile strength beyond the yield point. In this way, the resistance is reduced during the period of plastic deformation. The membrane 403 is also relatively thinner than either the frame 401 or the drive transfer elements 404a, 404b, 404c and provides minimal resistance to future motions conveyed by the drive transfer elements 404*a*, 404*b*, 404*c*.

To further reduce the resistance on the drive transfer elements 404*a*, 404*b*, 404*c* from the membrane 403, the length of the drive paths, compared to distance between adjacent drive paths may be minimized. Preferably, the length of each of the adjacent drive paths is less than five times the distance between the adjacent drive paths. Similarly, to further reduce the resistance on the drive transfer elements 404*a*, 404*b*, 404*c* from the membrane 403, the length of the drive paths, compared to distance between the frame 401 and the adjacent drive transfer element may be minimized. Preferably, the length of each of the adjacent drive paths is less than five times the distance between the frame 401 and the adjacent drive path. As a result of both options, there may be a larger area of membrane 403 which is able to stretch between the drive transfer element 404 and the adjacent component (the adjacent drive transfer element 404 or the frame 401) to which the drive transfer element 404 is moving relative. This may reduce the resistance on the drive transfer element 404. Another embodiment of the invention is illustrated in FIG. 8.

Figure 8:
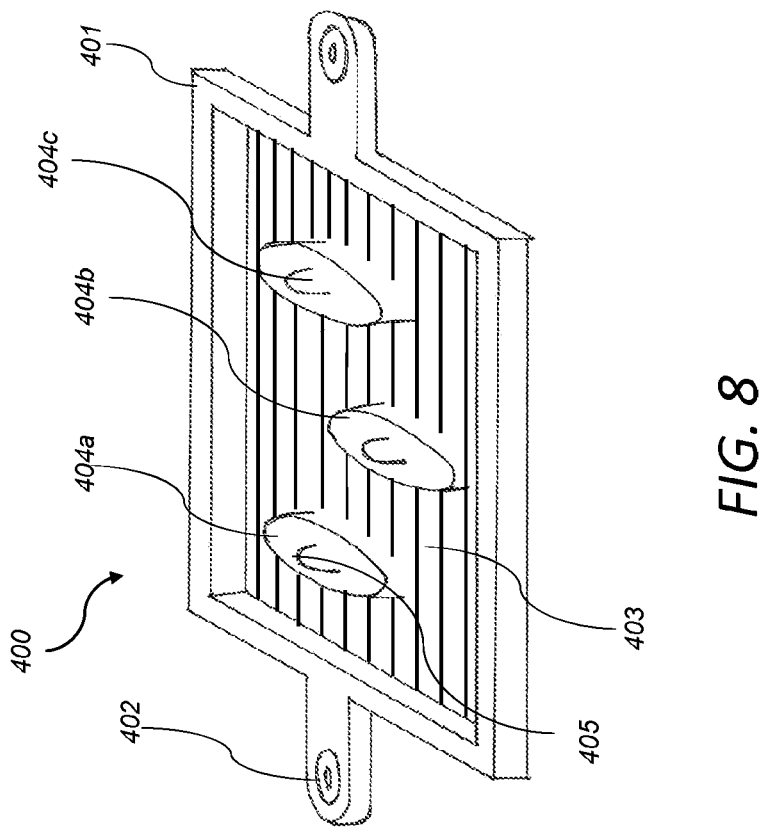
FIG. 8 illustrates a perspective view of a drape interface structure of a second embodiment.

As shown in FIGS. 4 and 8, the drive transfer element 404 is surrounded by the membrane 403 and held within the membrane 403. In this way, the drive transfer element 404 may be held in an initial position. In the initial position, the drive transfer element 404 is supported by the tension in the membrane 403. The membrane 303 is in a strained state in which tensile forces from the membrane 403 hold the drive transfer element 404 in place. In implementations where the membrane 403 is planar, this may hold or support the drive transfer element 404 substantially in the plane of the membrane 403.

Any movement of the drive transfer element 404 in the membrane 403 would need to overcome the tension provided by the membrane 403. As such, driving the drive transfer element 404 in the membrane 403 would need significant force. The tension force from the membrane 403 can also be inconsistent. High and/or inconsistent tension force from the membrane 403 can add additional loading on the driving elements and can make it difficult to control the position of the driving elements. The increased loading on the drive transfer elements can also result in less cable tension in the instrument 103 for a given motor torque. Additionally, increasing the tension in the membrane 403 can increase the likelihood of tearing of the membrane 403. The tension can be particularly high when two drive transfer elements 404 are at opposite ends of travel, or are both a long way from their respective starting positions. Alternatively, tension can be particularly high in rotary drive when drive transfer elements 404 turn by a large angle. It can therefore be advantageous to reduce the level of tension in the membrane 403.

As described herein, the drive transfer element 404 can be driven within the membrane 403. As the membrane 403 is constrained by the frame 401, movements in the membrane 403 are movements relative to the frame 401. The membrane 403 is configured to have a lower resistance on the movement of the drive transfer element 404 in a direction along the drive path. The membrane 403 is also configured to have a higher resistance on the movement of the drive transfer element 404 in a direction not along the drive path. This is illustrated by the lines in the membrane 403 in FIG. 8. As a result, when the drive transfer element 404 is driven along the drive path, then the resistance from the membrane 403 is less than if the drive transfer element 404 were to be driven in a different direction which is not along the drive path. It is possible that the membrane 403 may be configured to have other directions in which resistance is at a lower level. For example, the resistance in directions close to the drive path may have similarly low resistance levels. However, the resistance in the direction of the drive path is lower than the resistance in at least one direction not in the direction of the drive path.

Preferably, the resistance on the movement of the drive transfer element 404 in the direction along the drive path is the lowest level of resistance of all of the directions within the membrane 403. For example, once the angle of the direction of the drive transfer element 404 moves away from the drive path, then the level of resistance may increase. In particular, membrane 403 may be configured to have increasing resistance on the movement of the drive transfer element 404 with respect to the angle of the direction of movement of the drive transfer element 404 from the drive path. Merely by way of example, if the angle of the direction of movement of the drive transfer element 404 is 0° then it may have a lower resistance than 15°, which may in turn have a lower resistance than 30°. The increase in resistance with respect to angle of the direction of movement of the drive transfer element 404 from the drive path may increase linearly. Alternatively, increase in resistance with respect to angle of the direction of movement of the drive transfer element 404 from the drive path may increase non-linearly, for example as defined by function of angle. The relation between the resistance and the angle of the direction of movement of the drive transfer element 404 from the drive path may depend on the configuration of the membrane 403.

Preferably, the membrane 403 is configured to have the highest level of resistance on the movement of the drive transfer element 404 in a direction perpendicular to the drive path. In other words, if the drive transfer element 404 is moved in a direction significantly from the drive path, then the resistance will be significantly higher. As described herein, as the level of resistance may increase with the angle of the direction of movement of the drive transfer element 404 from the drive path, the level of resistance may be a maximum in a direction 90° from the drive path. The level of resistance may increase with angle of the direction of movement of the drive transfer element 404 from the drive path between 0° and 90°. The level of resistance may decrease with angle of the direction of movement of the drive transfer element 404 from the drive path between 90° and 180°.

Although the level of resistance may be higher in directions which angle away from the direction of movement of the drive transfer element 404, it can be preferable that the level of resistance in all directions is substantially lower that the force available to drive the drive transfer elements 404. In this way, any movement of the drive transfer element 404 should not be significantly resisted by the membrane 403.

As shown in FIGS. 7*a* and 7*b*, and as described herein, the membrane 403 may comprise a thin-skinned structure. Preferably, the drive transfer element 404 is configured to be driven in the plane of the thin-skinned membrane 403. As such, the variation of the resistance with angle of the direction of movement of the drive transfer element 404 from the drive path may be in the plane of the membrane 403. For example, a movement perpendicular to the drive path would be in the plane of the membrane 403 at 90° from the drive path. However, in embodiments where the membrane 403 is not thin-skinned and/or planar, the resistance may also vary with angle of the direction of movement of the drive transfer element 404 from the drive path, in which the angle is with respect to the plane of the drive path. For example, the resistance may increase if the drive transfer element 404 moves above or below the membrane 403.

It may be advantageous to provide a lower resistance in the direction along the drive path and a higher resistance in a direction not along the drive path. For example, a lower resistance along the drive path may reduce the resistance on the drive transfer element 404 during operation, i.e. when the drive transfer element 404 is being driven along its operating path. This may reduce the loading on the driving elements which may also make it easier and more accurate to control the position of the driving element. Additionally, a higher resistance in a direction not along the drive path may force the drive transfer element 404 to be pushed back to its operating path, i.e. if the drive transfer element 404 has been displaced from the drive path. The increased loading on the driving elements from the increase resistance may also provide feedback to the control system 106 that the drive transfer element 404 is not on the operating path.

The membrane 403 may comprise a material that is configured to have a lower resistance on the movement of the drive transfer element 404 in a direction along the drive path. The material may also be configured to have a higher resistance on the movement of the drive transfer element 404 in a direction not along the drive path. In other words, the variation in the resistance with respect to angle of the direction of movement of the drive transfer element 404 from the drive path may be due to the material of the membrane 403. To achieve this, the properties of the material may be varied in different directions. For example, the material may be configured to have higher elasticity in the direction of the drive path, and a have lower elasticity in directions not in the direction of the drive path.

In particular, the material may have anisotropic properties. As an example, the material may comprise a laminated structure. For example, a polymer and/or composite structure. The laminated structure may be layered up in such a way that the more flexible structures run in the direction of the drive path, and the stiffer structures run in the direction perpendicular to the drive path. For example, the laminated structure may be layered up in such a way that the fibres of the material run in the direction perpendicular to the drive path, so that the fibres may be pulled apart in the direction of the drive path, which may result in lower resistance. In particular, the membrane 403 may comprise a substrate layer, adhesive layer, and a capping layer sandwiched together. Further layers of each type of layer may be used to build up the thickness and/or alter the properties of the membrane 403. It will be appreciated that there may be other techniques for providing anisotropic properties to a material.

The membrane 403 may comprise a structure that is configured to have a lower resistance on the movement of the drive transfer element 404 in a direction along the drive path. The structure may also be configured to have a higher resistance on the movement of the drive transfer element 404 in a direction not along the drive path. In other words, the variation in the resistance with respect to angle of the direction of movement of the drive transfer element 404 from the drive path may be due to the structure of the membrane 403. To achieve this, the arrangement of the structure may be varied in different directions. For example, the structure may be configured to have higher elasticity in the direction of the drive path, and a have lower elasticity in directions not in the direction of the drive path.

As an example, the membrane 403 may comprise corrugations running in the direction perpendicular to the drive path. This may be illustrated by the lines in FIG. 8. In this way, the membrane 403 may be configured to fold up when the drive transfer element 404 is driven along the drive path. The folding of the membrane 403 may provide significantly lower resistance than stretching the membrane 403 material itself. As such, if the drive transfer element 404 were to move perpendicular the drive path, then the resistance would be significantly higher.

The membrane 403 may comprise a material and a structure that is configured to have a lower resistance on the movement of the drive transfer element 404 in a direction along the drive path. The material and the structure may also be configured to have a higher resistance on the movement of the drive transfer element 404 in a direction not along the drive path. In other words, the variation in the resistance with respect to angle of the direction of movement of the drive transfer element 404 from the drive path may be due to the material and the structure of the membrane 403. To achieve this, the properties of the material and the arrangement of the structure may be varied in different directions. For example, the material and the structure may be configured to have higher elasticity in the direction of the drive path, and a have lower elasticity in directions not in the direction of the drive path. As a result of varying both the material and the structure of the membrane 403, there may be further scope for fine tuning the resistance with respect to angle of the direction of movement of the drive transfer element 404 from the drive path.

As described herein with reference to FIG. 4, the drape interface structure 400 may comprise more than one drive transfer element 404. FIG. 4 shows three drive transfer elements 404a, 404b, 404c. The membrane 403 is configured to have a lower resistance on the movement of each of the drive transfer elements 404a, 404b, 404c in a direction along the respective drive paths. The membrane 403 is also configured to have a higher resistance on the movement of each of the drive transfer elements 404a, 404b, 404c in a direction not along the respective drive paths. This is illustrated by the lines in the membrane 403 in FIG. 6. As a result, when each of the drive transfer elements 404a, 404b, 404c are driven along their respective drive paths, then the resistance from the membrane 403 is less than if each of the drive transfer elements 404a, 404b, 404c were to be driven in a different direction which is not along their respective drive path.

As described herein, the each of the drive transfer elements 404a, 404b, 404c may move along a respective drive path. In the case of parallel drive paths, the membrane 403 may be configured to have a lower resistance in the direction of all the drive paths. In this way, each of the drive transfer elements 404a, 404b, 404c may be provided with the lower resistance. However, in embodiments in which the respective drive paths are not parallel, the direction of lower resistance may only align with one or more of the drive paths. For example, if there are three the drive transfer elements 404a, 404b, 404c each with drive paths in different directions, then the direction of lower resistance may be aligned with one of the drive transfer elements 404a, 404b, 404c. Preferably, the drive transfer element 404a, 404b, 404c selected to have the lowest resistance from the membrane 403 may be the drive transfer element 404a, 404b, 404c with the longest range of travel, or highest amount of operational use. Alternatively, the membrane 403 may be configured such that, even if the drive paths are not parallel, the membrane 403 still has a low level of resistance for each of the drive transfer elements 404a, 404b, 404c. For example, the membrane 403 may comprise regions for each of the drive transfer elements 404a, 404b, 404c in which the resistance on the individual drive transfer element 404a, 404*b*, 404*c* in the direction of movement is lower and the resistance on the individual drive transfer element 404*a*, 404*b*, 404*c* not in the direction of movement is higher.

To further reduce the resistance on the drive transfer elements 404*a*, 404*b*, 404*c* from the membrane 403, the length of the drive paths, compared to distance between adjacent drive paths may be minimized. Preferably, the length of each of the adjacent drive paths is less than five times the distance between the adjacent drive paths. Similarly, to further reduce the resistance on the drive transfer elements 404*a*, 404*b*, 404*c* from the membrane 403, the length of the drive paths, compared to distance between the frame 401 and the adjacent drive transfer element may be minimized. Preferably, the length of each of the adjacent drive paths is less than five times the distance between the frame 401 and the adjacent drive path. As a result of both options, there may be a larger area of membrane 403 which is able to stretch between the drive transfer element 404 and the adjacent component (the adjacent drive transfer element 404 or the frame 401) to which the drive transfer element 404 is moving relative. This may reduce the resistance on the drive transfer element 404.

The general principles defined herein may be applied to other embodiments and applications without departing from the spirit and scope of the present invention. Thus, the present invention is not intended to be limited to the embodiments shown, but is to be accorded the widest scope consistent with the principles and features disclosed herein.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description, it will be evident to a person skilled in the art that various modifications may be made within the scope of the invention.

The invention claimed is:

1. A drape interface structure comprising:
a frame defining an opening;
a membrane spanning the opening of the frame;
a drive transfer element attached to the membrane and adapted to convey motion through the membrane;
wherein the membrane is of a material that can deform to form a plastically deformed region in the membrane in response to an initial movement of the drive transfer element relative to the frame, such that subsequent movements of the drive transfer element in the membrane have reduced resistance from the membrane; and
wherein the membrane can deform, in response to the initial movement of the drive transfer element, to form the plastically deformed region such that the membrane surrounding the plastically deformed region is not plastically deformed.

2. A drape interface structure as claimed in claim 1, comprising one or more further drive transfer elements, each further drive transfer element being attached to the membrane and adapted to convey motion through the membrane, and optionally wherein the one or more further drive transfer elements are adapted to convey motion through the membrane along respective drive paths, and the respective drive paths of the drive transfer elements are parallel to one another, and optionally wherein the membrane can deform to form respective further plastically deformed regions in the membrane in response to an initial movement of each of the further drive transfer elements relative to the frame, such that subsequent movements of each of the further drive transfer elements in the membrane have reduced resistance from the membrane.

3. A drape interface structure as claimed in claim 2, wherein the membrane can deform, in response to the initial movement of each of the drive transfer elements, to form the respective plastically deformed regions such that the respective plastically deformed regions do not overlap, or wherein the membrane can deform, in response to the initial movement of each of the drive transfer elements, to form the respective plastically deformed regions such that the respective plastically deformed regions do overlap.

4. A drape interface structure as claimed in claim 1, wherein a material of the drive transfer element comprises a non-elastomeric material.

5. A drape interface structure as claimed in claim 4, wherein the material of the drive transfer element comprises polyethylene and/or wherein a material of the frame comprises polyethylene.

6. A drape interface structure as claimed in claim 1, wherein the membrane is substantially taut such that the drive transfer element is held in the membrane.

7. A drape interface structure as claimed in claim 1, wherein the membrane can deform, in response to the initial movement of the drive transfer element a distance along a drive path, to form the plastically deformed region having a length along the drive path of at least half of the distance moved along the drive path, and optionally wherein the membrane can deform, in response to the initial movement of the drive transfer element along a drive path, to form the plastically deformed region having a width perpendicular to the drive path of at least the width of the drive transfer element.

8. A drape interface structure as claimed in claim 1, wherein the membrane can deform such that the subsequent movements of the drive transfer element in the membrane have substantially no resistance from the membrane.

9. A drape interface structure as claimed in claim 1, wherein the membrane can deform such that the subsequent movements of the drive transfer element in the plastically deformed region have reduced resistance from the membrane.

10. A drape interface structure as claimed in claim 1, wherein the drive transfer element comprises a recess on a first side of the membrane and a protrusion on the second side of the membrane, and optionally wherein the drive transfer element recess is engageable with an interface protrusion, and the drive transfer element protrusion is engageable with an interface recess.

11. A drape interface structure as claimed in claim 1, wherein the frame comprises a securing fitting configured to secure the frame to a robot arm.

12. A drape interface structure as claimed in claim 1, wherein the drive path is linear.

13. A drape interface structure as claimed in claim 1, wherein the frame and the drive transfer element are heat welded to the membrane.

14. A drape interface structure as claimed in claim 1, wherein a material of the membrane is a thermoplastic polymer, and optionally wherein the thermoplastic polymer material of the membrane comprises one or more of high-density polyethylene or linear low-density polyethylene.

15. A drape interface structure comprising:

a frame defining an opening;

a membrane spanning the opening of the frame;

a drive transfer element attached to the membrane and adapted to convey motion along a drive path through the membrane;

wherein the membrane is configured to have a lower resistance on movement of the drive transfer element in a direction along the drive path and a higher resistance on movement of the drive transfer element in a direction not along the drive path, and wherein the membrane comprises a material and/or structure that is configured to have a lower resistance on movement of the drive transfer element in a direction along the drive path and a higher resistance on movement of the drive transfer element in a direction not along the drive path.

16. A drape interface structure as claimed in claim 15, wherein the membrane comprises an anisotropic material.

17. A drape interface structure as claimed in claim 15, wherein the membrane is configured to have a highest resistance on movement of the drive transfer element in a direction perpendicular to the drive path, and optionally wherein the membrane is configured to have an increasing resistance on movement of the drive transfer element with respect to an angle of the direction of movement of the drive transfer element from the drive path.

18. A drape interface structure as claimed in claim 15, comprising one or more further drive transfer elements, each further drive transfer element being attached to the membrane and adapted to convey motion through the membrane along a respective drive path, and optionally wherein respective drive paths of the drive transfer elements are parallel to one another, and optionally wherein the membrane is configured to have a lower resistance on movement of each of the further drive transfer elements in a direction along the respective drive paths and a higher resistance on the movement of each of the further drive transfer elements in a direction not along the respective drive paths.

* * * * *